United States Patent
DeSoutter et al.

(10) Patent No.: US 11,464,524 B2
(45) Date of Patent: Oct. 11, 2022

(54) COUPLING MECHANISM FOR A SURGICAL DEVICE

(71) Applicant: Zethon Limited, Buckinghamshire (GB)

(72) Inventors: William DeSoutter, Buckinghamshire (GB); Toby Courtney, Buckinghamshire (GB)

(73) Assignee: Zethon Limited, Buckinghamshire (GB)

( * ) Notice: Subject to any disclaimer, the term of this patent is extended or adjusted under 35 U.S.C. 154(b) by 175 days.

(21) Appl. No.: 16/614,028

(22) PCT Filed: May 15, 2018

(86) PCT No.: PCT/EP2018/062586
§ 371 (c)(1),
(2) Date: Nov. 15, 2019

(87) PCT Pub. No.: WO2018/210858
PCT Pub. Date: Nov. 22, 2018

(65) Prior Publication Data
US 2020/0069316 A1 Mar. 5, 2020

(30) Foreign Application Priority Data
May 15, 2017 (GB) .................................. 1707751

(51) Int. Cl.
*A61B 17/16* (2006.01)
*A61B 17/00* (2006.01)
(Continued)

(52) U.S. Cl.
CPC ........ *A61B 17/162* (2013.01); *A61B 17/1633* (2013.01); *A61B 17/1622* (2013.01);
(Continued)

(58) Field of Classification Search
CPC ... A61B 17/162; A61B 17/16; A61B 17/1633; A61B 17/1622; A61B 2017/0046;
(Continued)

(56) References Cited

U.S. PATENT DOCUMENTS

| 4,184,692 A | 1/1980 | Benson et al. |
| 5,013,194 A | 5/1991 | Wienhold |

(Continued)

OTHER PUBLICATIONS

International Searching Authority, "International Preliminary Report on Patentability for PCT Application No. PCT/EP2018/062586", Foreign Counterpart to U.S. Appl. No. 16/614,028, dated Nov. 15, 2019, pp. 1-7, Published in: WO.
(Continued)

*Primary Examiner* — Marcela I. Shirsat
(74) *Attorney, Agent, or Firm* — Dorsey & Whitney LLP

(57) ABSTRACT

A surgical tool-piece and a coupling mechanism for a surgical tool-piece are provided. The surgical tool-piece is configured to be driving by a driving mechanism. The surgical tool-piece comprises a shaft having a longitudinal axis running from a distal end of the shaft to a coupling portion at a proximal end of the shaft. The coupling portion comprises a driving section comprising at least three indentations located around the circumference of the coupling portion, each indentation being configured to receive a corresponding driving element of the driving mechanism to secure the tool-piece both longitudinally and rotationally.

12 Claims, 13 Drawing Sheets

(51) Int. Cl.
*A61C 17/02* (2006.01)
*B23B 31/107* (2006.01)
*A61C 1/14* (2006.01)

(52) U.S. Cl.
CPC ............... *A61B 2017/00464* (2013.01); *A61B 2017/00477* (2013.01); *A61C 1/144* (2013.01); *A61C 17/0202* (2013.01); *B23B 31/107* (2013.01); *B23B 31/1071* (2013.01); *B23B 31/1072* (2013.01)

(58) Field of Classification Search
CPC ........... A61B 2017/00464; A61B 2017/00477; B23B 31/201; B23B 31/1072; B23B 31/1071; B23B 31/107; A61C 1/144; A61C 17/0202
USPC .......................................................... 606/80
See application file for complete search history.

(56) References Cited

U.S. PATENT DOCUMENTS

| 5,222,956 | A | | 6/1993 | Waldron | |
|---|---|---|---|---|---|
| 5,888,200 | A | * | 3/1999 | Walen | B25F 3/00 606/167 |
| 6,562,055 | B2 | | 5/2003 | Walen | |
| 8,597,316 | B2 | * | 12/2013 | McCombs | A61B 17/1628 606/167 |
| 2003/0023256 | A1 | * | 1/2003 | Estes | A61B 17/1633 606/167 |
| 2015/0313610 | A1 | * | 11/2015 | Edwards | A61B 17/16 606/80 |

OTHER PUBLICATIONS

Examination Report dated Nov. 13, 2017 in connection with British Patent Application No. 1707751.2, 8 pages.

* cited by examiner

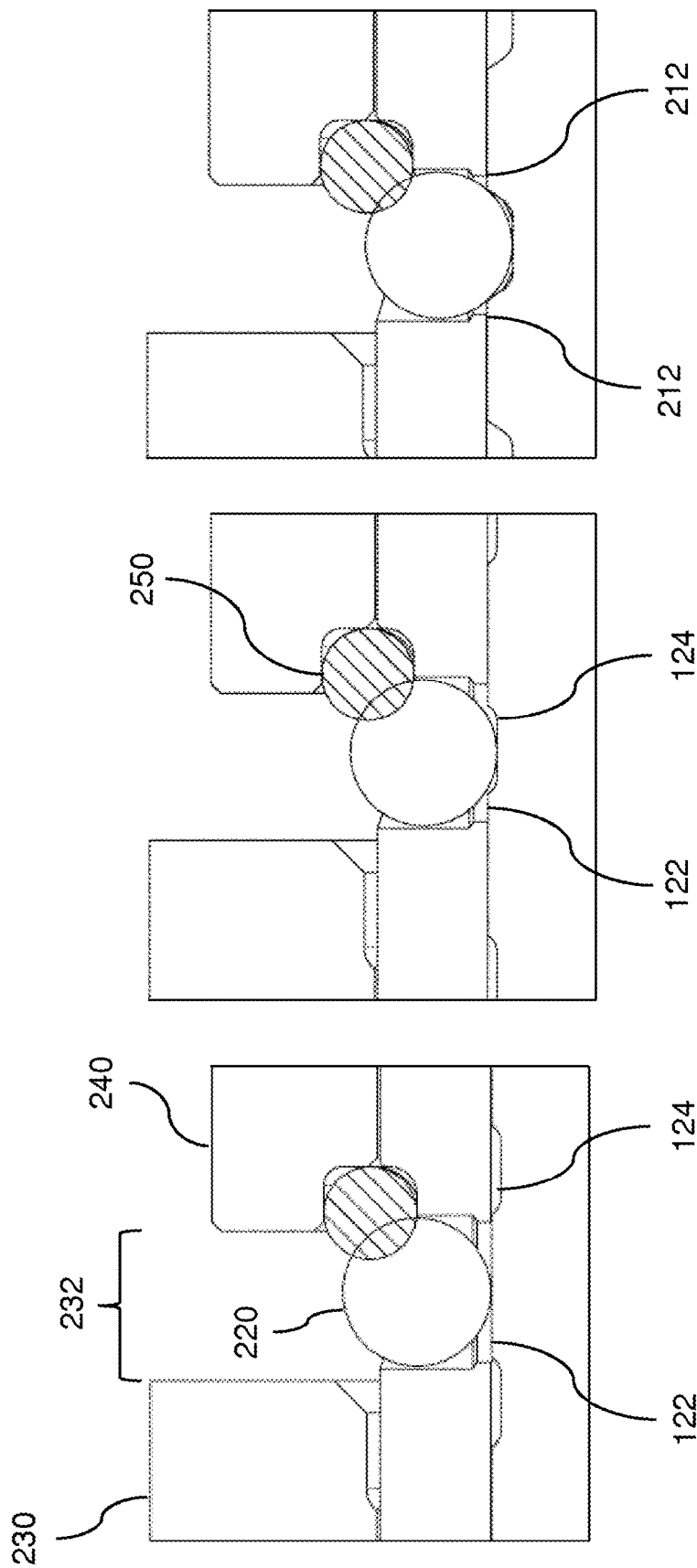

COUPLING MECHANISM FOR A SURGICAL DEVICE

This application is a National Stage Entry of International Patent Application No. PCT/EP2018/062586, filed May 15, 2018, entitled "COUPLING MECHANISM FOR A SURGICAL DEVICE," which claims priority to United Kingdom Patent Application No. 1707751.2, filed May 15, 2017, entitled "COUPLING MECHANISM FOR A SURGICAL DEVICE", each of which is incorporated by reference herein, in the entirety and for all purposes.

TECHNICAL FIELD

The present disclosure relates to surgical tool-pieces and coupling mechanisms for securing surgical tool-pieces. In particular, but without limitation, this disclosure relates to surgical tools and coupling mechanisms for surgical tools.

BACKGROUND

During surgical procedures, it is often necessary to cut bone or other tissue. To this end, pneumatically or electrically powered surgical drills and burs may be utilised. These surgical tools often comprise a handpiece for driving a tool-piece comprising a cutting portion. The tool-piece is a cutting means whilst the handpiece is a driving means.

It is often necessary to replace the tool-piece after use as it may become contaminated and the cutting portion may be dulled. Accordingly, the handpiece may comprise a releasable locking mechanism into which a tool-piece may be releasably coupled to allow it to be driven by the handpiece. This allows the tool-pieces to be replaced once used to avoid contamination. This also allows the same handpiece to drive a variety of different types of interchangeable tool-piece, each having a different function.

Different tool-pieces may have different cutting ends. For instance, a tool-piece may have a drill head or a bur at its end. Different tool-pieces may also have different sized cutting ends for use in different procedures. Furthermore, different tool-pieces may have different lengths of shaft (different longitudinal lengths), depending on the location of the intended surgical site and the surgical procedure being performed.

Each tool-piece may comprise a locking portion for coupling to a locking mechanism of the handpiece or some other driving mechanism. There are generally two types of locking mechanism: non-adjustable mechanisms, and adjustable mechanisms.

Non-Adjustable Mechanisms

A non-adjustable tool-piece has a single longitudinal location at which it may be coupled to a driving mechanism. One method for locking the tool-piece in place is to have a single rotational groove set into the shaft of the tool-piece. This groove may be square or circular. The groove is used to lock the tool-piece longitudinally to the locking mechanism, possibly through a set of balls. No torque is transmitted through this mechanism.

A drive dog may be placed at the drive end of the tool-piece. This dog usually comprises at least one flat surface for driving the tool-piece. A mating part, on the bur locking mechanism is used to locate the tool-piece rotationally. The torque from the motor is driven through this drive dog.

Whilst a strong driving force may be provided through non-adjustable mechanisms, these mechanisms do not allow tool-pieces to be adjusted along their longitudinal length. In addition, drive dog mechanisms with fewer flat surfaces are more difficult to align rotationally, as the number of possible alignment positions is proportional to the number of driving surfaces. For instance, one flat surface provides one rotational alignment position and two flat surfaces provide two alignment positions.

Furthermore, these mechanisms lock the longitudinal location of tool-piece using a separate feature (e.g. the groove) to that which drives the tool-piece (e.g. a drive dog). Accordingly, this type of arrangement requires a more complicated coupling mechanism (as two separate mechanisms are required).

Adjustable Mechanisms

An adjustable locking mechanism has multiple longitudinal locations at which it may be coupled to a driving mechanism. There are a number of methods for achieving an adjustable tool-piece.

One mechanism provides a bur that includes a set of ridges, which are set on two flat surfaces 180° opposed to one another. As the bur is inserted into a driving mechanism, location prongs in the driving mechanism ride over the ridges.

Whilst this type of mechanism allows the bur to be adjusted longitudinally, its drive dog has only two flat surfaces, which makes it difficult to align rotationally. In addition, the bur receives securing forces in one direction only, meaning that it is liable to jump to one side when being driven.

A different mechanism provides a bur comprising a set of countersunk grooves. The grooves and ridges of the bur are cylindrical. The drive is taken through the curved surface of one of the grooves using a collet system.

Whilst this type of bur may be adjusted longitudinally (via the selection of one of the grooves) and rotationally (as the surface is cylindrical), it is difficult to get sufficient torque through the drive mechanism due, in part, to the system driving via the cylindrical surface.

There is therefore a need for a tool-piece and corresponding driving mechanism that provides a secure locking mechanism to allow the tool-piece to be driven effectively. In particular, there is a need for a mechanism that can be easily axially located in one position or scaled up to allow multiple longitudinal positions, whilst still being easy to align axially.

BRIEF DESCRIPTION OF THE DRAWINGS

Embodiments of the present invention will be understood and appreciated more fully from the following detailed description, made by way of example only and taken in conjunction with drawings in which:

FIGS. 9A, 9B and 9C show cross-sectional views of the coupling mechanism with the bur inserted within the mechanism at various depths;

SUMMARY OF INVENTION

Figure 1:
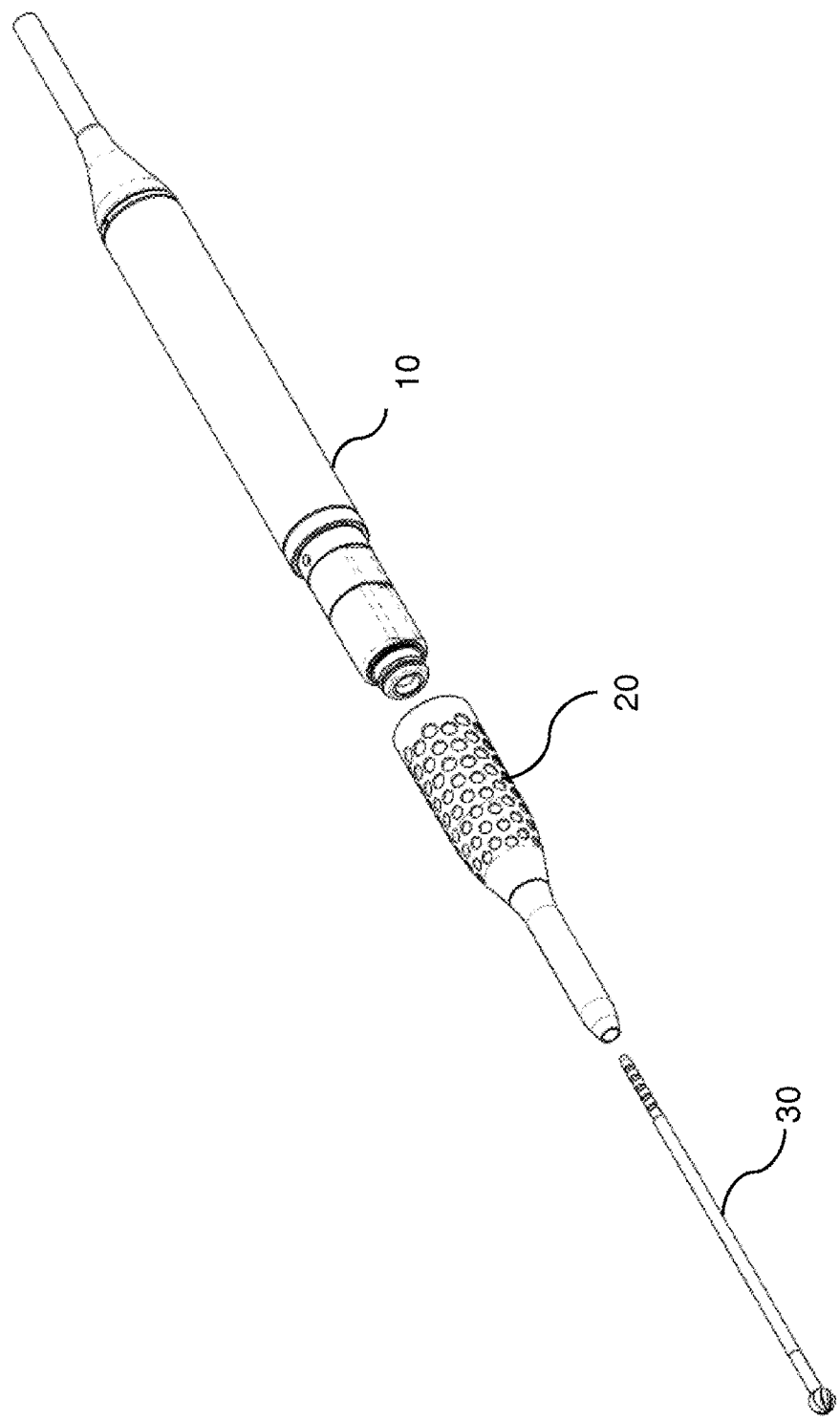
FIG. 1 shows a handpiece, nosepiece and bur according to an embodiment.

According to a first aspect of the invention there is provided a coupling mechanism for securing a surgical tool-piece, the coupling mechanism comprising a sheath forming an internal longitudinal cavity for receiving a coupling section of the tool-piece, the internal longitudinal cavity defining a central longitudinal axis of the coupling mechanism, and at least three opposing coupling elements configured to secure the tool-piece in the coupling mechanism. Each coupling element is located radially away from the central longitudinal axis and is configured to move radially outwards to allow at least part of the coupling section of the tool-piece to pass the coupling element. The coupling mechanism is configured to urge the coupling elements radially inwards towards the central longitudinal axis to secure the tool-piece longitudinally and rotationally at corresponding indentations in the coupling section of the tool-piece so that the tool-piece may be rotationally driven around the central longitudinal axis.

Driving a tool-piece via three coupling elements allows the tool-piece to be inserted into the mechanism in a greater number of rotational arrangements. This makes it easier to insert the tool-piece into the coupling mechanism. It also provides more secure driving and coupling as the driving elements secure the bur along a greater number of directions.

The driving elements act to secure the tool-piece both longitudinally and rotationally. Accordingly, the driving elements solve dual functions: to prevent the tool-piece moving longitudinally relative to the coupling mechanism once secured, and to secure the tool-piece rotationally (relative to the coupling mechanism) so that it may be rotationally driven by the coupling mechanism. This avoids the need for separate mechanisms for longitudinally locating the tool-piece and driving the tool-piece. It also allows the coupling mechanism to secure the tool-piece at a variety of longitudinal locations (if these locations are provided on the tool-piece). Accordingly, this provides a securing mechanism of reduced complexity that is adjustable to secure a tool-piece at multiple selectable longitudinal positions.

Advantageously, the at least three coupling elements may be substantially equally spaced around the central longitudinal axis from each other. This can help to secure and drive the tool-piece more evenly. Substantially evenly spaced could include some error on the spacing, such as ±5° or ±10°. In the case where there are three driving elements, the driving elements may be spaced about 120° around the central longitudinal axis from each other. The driving elements may be all located in line with each other, i.e. along a single plane that is perpendicular to the central longitudinal axis.

According to a further embodiment, the coupling elements are balls located within channels running radially through the sheath. This allows the balls to roll easily over protrusions along the tool-piece to make insertion of the tool-piece easier.

According to a further embodiment the coupling mechanism comprises an O-ring configured to urge the balls radially inwards towards the central longitudinal axis. Any urging means may be utilised to urge the driving elements inwards; however, an O-ring provides the advantage that it can act as the urging means for all balls at the same time, by encircling all of the balls. The O-ring can be positioned to prevent the balls from moving too far outwards or, in the extreme event, entirely falling out of the coupling mechanism.

According to a further embodiment, the coupling mechanism further comprises a locking ring configured to pass over the balls when the balls are located within the corresponding indentations in the tool-piece to lock the balls within the indentations to secure the tool-piece within the coupling mechanism. This provides an effective mechanism for locking the tool-piece in place. The locking ring can also provide an additional urging force inwards against the balls when it is pushed against the outer edges of the balls. This can help to move the balls into position for securing the tool-piece.

According to a further embodiment, the locking ring is configured such that it cannot pass over balls until the balls are fully inserted into the indentations of the tool-piece. This can help to prevent the coupling mechanism to be locked before the tool-piece is effectively secured in the mechanism.

According to a further embodiment, the coupling mechanism comprises one or more protrusions at the inner end of each of the channels. The one or more protrusions are configured to prevent the corresponding balls from passing fully into the internal longitudinal cavity. The one or more protrusions may be a lip or flange or a narrowing of the corresponding channel at the inner end of the channel.

According to an embodiment there is provided a surgical tool comprising a coupling mechanism according to any of the above embodiments and a motor configured to drive the coupling mechanism to rotate around the central longitudinal axis.

According to a second aspect of the invention there is provided a surgical tool-piece configured to be driven by a driving mechanism, the tool-piece comprising a shaft having a longitudinal axis running from a distal end of the shaft to a coupling portion at a proximal end of the shaft. The coupling portion comprises a driving section comprising at least three indentations located around the circumference of the coupling portion, each indentation being configured to receive a corresponding driving element of the driving mechanism to secure the tool-piece both longitudinally and rotationally.

As with the driving mechanism, a tool-piece that has three or more indentations can be driven more effectively and can be more easily located within a coupling mechanism due to an increased number of rotational arrangements. The indentations are configured to secure the tool-piece both longitudinally and rotationally. Accordingly, this avoids the need for separate sections to longitudinally locating the tool-piece and rotationally securing and driving the tool-piece. As the indentations longitudinally secure the tool-piece, the tool-piece can be easily adapted to include multiple coupling/driving sections longitudinally spaced apart from each other to allow the longitudinal position of the tool-piece to be adjusted. The coupling portion may be cylindrical at portions not comprising the indentations (e.g. substantially cylindrical). This can make the tool-piece easier to insert into a coupling mechanism it can be inserted along any rotational alignment.

According to one embodiment, the distal end comprises a tool portion. This could comprise a cutting portion, such as a bur, drill or blade, or any other portion for conferring the driving force provided by the driving mechanism.

According to one embodiment the at least three indentations are substantially equally spaced from each other around the circumference of the shaft. This can help to secure and drive the tool-piece more evenly. Substantially evenly spaced could include some error on the spacing, such as ±5° or ±10°. In the case where there are three indentations, the indentations may be spaced about 120° around the central longitudinal axis from each other. The indentations may be all located in line with each other, i.e. along a single plane that is perpendicular to the central longitudinal axis.

According to one embodiment, each indentation comprises one or more surfaces, wherein each of the one or more surfaces is are configured to receive a driving force to drive the surgical tool-piece to rotate around the longitudinal axis.

According to a further embodiment, each of the one or more surfaces defines a corresponding flat surface that passes along a first direction corresponding to the respective indentation, wherein the first direction is perpendicular to the longitudinal axis and the corresponding flat surface varies in radial distance from the longitudinal axis, increasing from a local minimum radial distance at a centre point of the indentation, when measured along the first direction. The first direction may be perpendicular to the longitudinal axis, but may not intersect the longitudinal axis. The varying radial distance allows the tool-piece to be secured within the indentation and rotationally driven against the one or more flat surfaces. The first direction may differ for each indentation.

According to a further embodiment, the one or more surfaces comprise a flat base of the respective indentation. Accordingly, a flat base may define a surface that has a varying radial distance from the longitudinal axis to allow the tool-piece to receive a rotational driving force via the flat base.

According to a further embodiment, each indentation is formed, at least partly, from respective distal and proximal walls configured to secure the surgical tool-piece longitudinally. Each distal and proximal wall may run, at least partially, circumferentially around the longitudinal axis. These walls may be specifically spaced apart to receive a driving element to allow the tool-piece to be effectively secured in the longitudinal direction. The walls may be sloped relative to the longitudinal axis and relative to the radial direction. This helps to make the insertion of the tool-piece into a driving mechanism easier, and provides additional faces against which the tool-piece may be driven.

According to a further embodiment, the one or more surfaces comprise one or both of the distal and proximal walls. Accordingly, the tool-piece may receive a rotational driving force via one or more of the flat base, the proximal wall or the distal wall. In one embodiment, the tool-piece is configured to receive a rotational driving force via the flat base, the proximal wall and the distal wall. In one embodiment, the flat face and the proximal and distal walls all run along the first direction.

According to a further embodiment, the distal and proximal walls are sloped at angles between 45° and 90° relative to the longitudinal axis. This range of angles has been found to be effective to allow the play off between ease of insertion of the tool-piece and strength of coupling. The slope of each wall can be considered the gradient, i.e. distal and proximal walls slope in opposite directions, away from each other. In one embodiment, the distal and proximal walls have substantially the same slope. This can help to provide a more balanced coupling mechanism. Having said this, alternative embodiments provide the distal and proximal walls having differing slopes.

According to a further embodiment, the distal and proximal walls are sloped at angles between 50° and 60° relative to the longitudinal axis. According to further embodiments, the distal and proximal walls are sloped at an angle of 55° relative to the longitudinal axis. This has been found to be the most effective angle for coupling the tool-piece whilst also providing effective haptic feedback to the user when the tool-piece is being inserted.

According to a further embodiment, the distal and proximal walls for each indentation are joined to form a channel running around the circumference of the tool-piece. The channel is formed from the indentations and channel sections linking adjacent the indentations in the driving location. Each channel section has a raised floor relative to its adjacent indentations to prevent the corresponding driving elements from moving along the channel, between indentations, without moving radially outwards.

By providing a channel that runs around the circumference, the user is provided with a means of correctly locating the tool-piece longitudinally even where the tool-piece is not correctly rotated. In addition, the raised floors provide means for urging the tool-piece into the correct orientation and to provide features upon which the tool-piece may be more securely driven.

According to a further embodiment, the indentations form a triangular cross-section taken along a plane running perpendicular to the longitudinal axis and passing through the channel. This provides an increased number of rotational arrangements whilst also providing large enough features to allow the tool-piece to be driven effectively. As the number of indentations/faces in the channel is increased, the driving location becomes more cylindrical, therefore reducing the size of the features upon which torque can be effectively applied. The triangular cross-section may have flat faces, that is, the indentations may have flat driving faces at their bases.

According to a further embodiment the raised sections form rounded corners for the triangular cross-section. This helps to provide a camming action to rotate the tool-piece into the correct rotational alignment when driving elements are urged against the corners. In addition, the rounded corners help to prevent the tool-piece from jamming within the coupling mechanism.

According to a further embodiment, the coupling portion comprises a plurality of driving sections separated longitudinally from each other along the coupling portion to allow the tool-piece to be selectively coupled to the driving mechanism at different longitudinal positions along the coupling portion. This allows the longitudinal position of the tool-piece to be adjusted based on the needs of the user. This means that one tool-piece may be able to serve the purpose that a number of different length tool-pieces may have otherwise been required. The indentations of different driving sections need not be located in same angular positions, although this can help the user to more easily position the tool-piece within the coupling mechanism.

According to a further embodiment, the driving sections are separated by intermediate sections, wherein the intermediate sections have a circular cross-section taken along a plane running perpendicular to the longitudinal axis. That is, the intermediate sections are cylindrical. This allows the tool-piece to be easily inserted into the coupling mechanism at any rotation.

According to a further embodiment, the proximal end of the shaft is conical or frusto-conical. This can help to ease driving members out of the way of the tool-piece, as well as allowing the tool-piece to be easily inserted at any rotation.

According to a further embodiment there is provided a kit of parts comprising a surgical tool-piece according to any of the above embodiments and a coupling mechanism according to any of the above embodiments.

According to a further embodiment there is provided a surgical tool comprising a surgical tool-piece according to any of above embodiments and a coupling mechanism according to any of the above embodiments.

DETAILED DESCRIPTION

Embodiments described herein provide a novel coupling mechanism for transmitting sufficient torque whilst allowing longitudinal adjustability in a compact footprint. This is suitable for driving any rotational tool, such as a bur or drill. Nevertheless, for simplicity, the following description shall relate to burs.

FIG. 1 shows a handpiece, nosepiece and bur according to an embodiment. The handpiece 10 comprises a coupling mechanism configured to secure and drive the bur 30. The nosepiece 20 fits over the coupling mechanism of the handpiece 10. The nosepiece 20 comprises a longitudinal channel configured to receive the bur 30 to stabilise the bur 30 as it is being driven by the handpiece 10.

In an alternative arrangement, the nosepiece 20 may provide a driving force to the bur 30. In this case, the nosepiece 20 comprises a coupling mechanism configures to secure and drive the bur 30. The nosepiece 20 in turn is coupled to the handpiece 10 that provides the driving force to the nosepiece 20. This can allow the nosepiece 20 to be bent to angle the bur 30 relative to the handpiece 10, thereby enabling access to sites that may be difficult to reach with a straight attachment.

Figure 2:
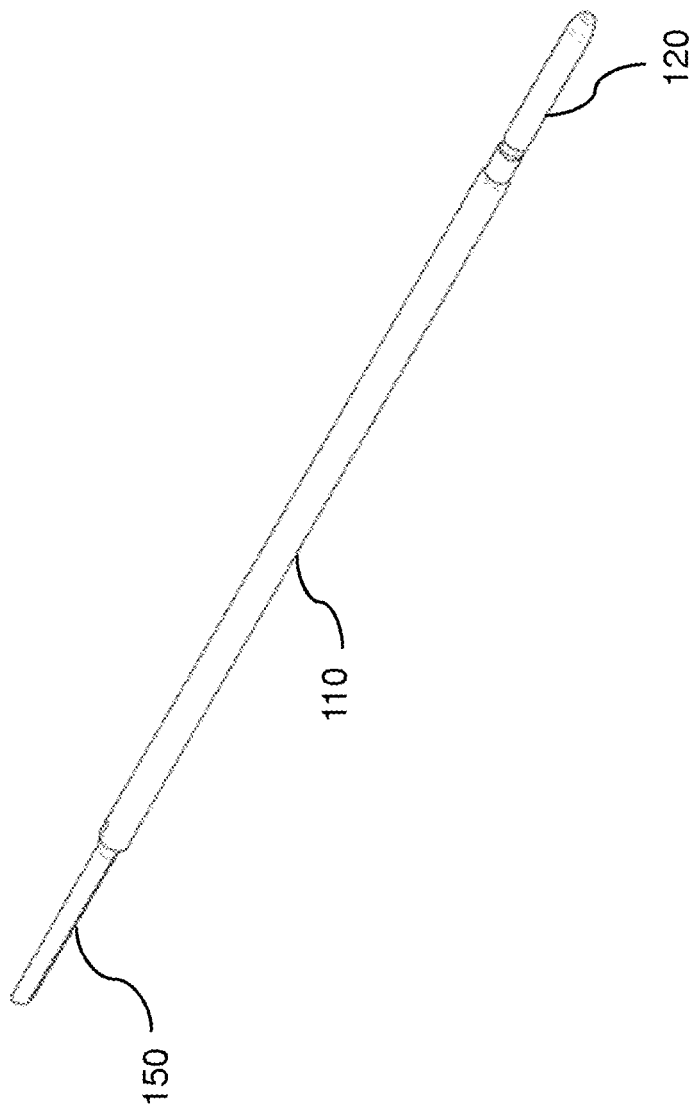
FIG. 2 shows a bur according to an embodiment.

FIG. 2 shows a bur according to an embodiment. The bur comprises a cylindrical shaft 110 with a coupling section 120 at a proximal end of the shaft 110 and a cutting end 150 at a distal end of the shaft 110. The shaft 110 defines a longitudinal axis of the bur.

The cutting end 150 comprises a bur portion. The bur portion may comprise a sharpened edges or an abrasive portion. In the present embodiment, the bur portion comprises an abrasive portion formed by a roughened surface, e.g. via a diamond coating. When the bur 10 is rotated around its longitudinal axis, the bur provides an abrasive action.

Coupling section 120 is configured to be coupled to a coupling mechanism. The coupling section 120 comprises a circumferential groove for receiving driving elements from a coupling mechanism. This allows the bur to be coupled to the coupling mechanism in a predefined longitudinal position (defined by the location of the groove).

Figure 3A:
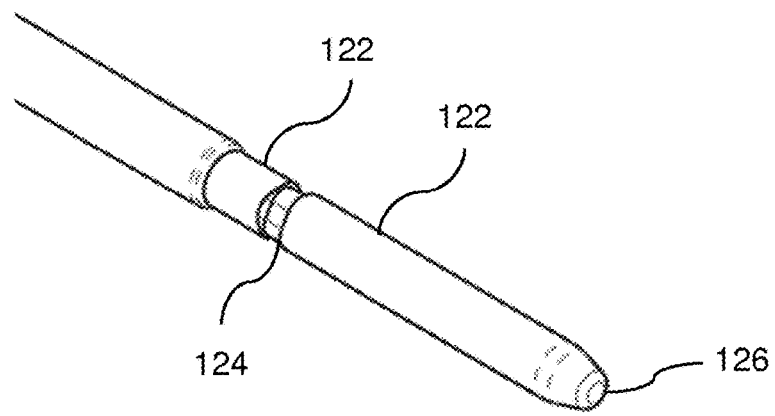
FIGS. 3A and 3B show enlarged views of the coupling section 120 of the bur of FIG. 2.
Figure 3B:
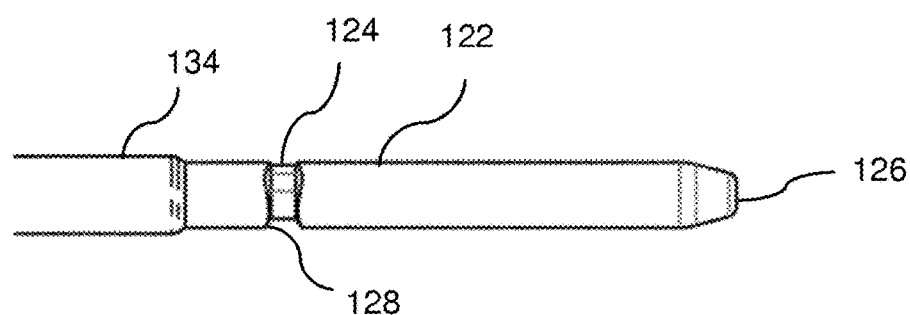
Figure 3C:
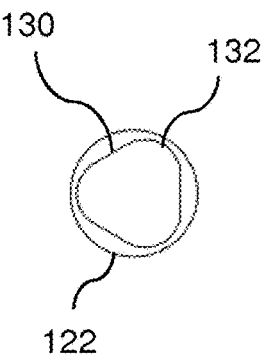
FIG. 3C shows a cross-sectional view of the coupling section 120 of FIG. 2.

FIGS. 3A and 3B show enlarged views of the coupling section 120 of the bur of FIG. 2. FIG. 3C shows a cross-sectional view of the coupling section 120 of FIG. 2. The coupling section 120 comprises a circumferential groove 124 flanked by two outwardly projecting circumferential ridges. The groove 124 and each ridge 122 run circumferentially around the coupling section 120.

The coupling section 120 terminates at a raised wall 134 that is configured to prevent the bur from being inserted too far into the coupling mechanism. The raised wall 134 runs circumferentially around the bur and projects radially outwards to a height equal to the circumference of the shaft 110. Accordingly, the entirety of the coupling section 120 has a reduced radius relative to the shaft 110.

The groove 124 forms a channel having a base that runs circumferentially around the coupling section 120. The base comprises three flat driving faces 130 against which the bur may be driven. The driving faces 130 are angled 120° relative to each other. The driving faces 130 therefore form a triangular cross-section with the longitudinal axis of the bur passing through the centre of the cross-section. The driving faces 130 are joined at rounded corners 132. The rounded corners 132 make the device easier to rotate when located inside a coupling mechanism.

The combination of the rounded corners 132 and the flat driving faces 130 results in the groove 124 having a variable depth (having a base of varying radial distance from the central longitudinal axis of the bur). It is deepest at the centre of each driving face 130, and shallowest at the corners 132. This means that the corners 132 form protrusions between the driving faces 130. This allows driving elements of a coupling mechanism to get purchase and rotationally drive the bur. The combination of the driving faces 130 and the corners 132 provide corresponding indentations for receiving the driving elements.

Whilst the rounded corners 130 form protrusions that separate the driving faces 130, they are still recessed relative to the ridges 122. This helps to urge the tool-piece into correct longitudinal alignment even when the driving elements are located above the corners 130. This also provides tactile feedback to the user regarding the various longitudinal positions at which the tool-piece may be coupled.

Each ridge 122 has a circular cross-section. This allows the bur to be inserted into the coupling mechanism in any rotational alignment. The coupling section 120 has a taper at its end (at the proximal end of the bur) to make insertion into the coupling mechanism easier. This taper forms a frusto-conical tip 126.

Figure 4A:
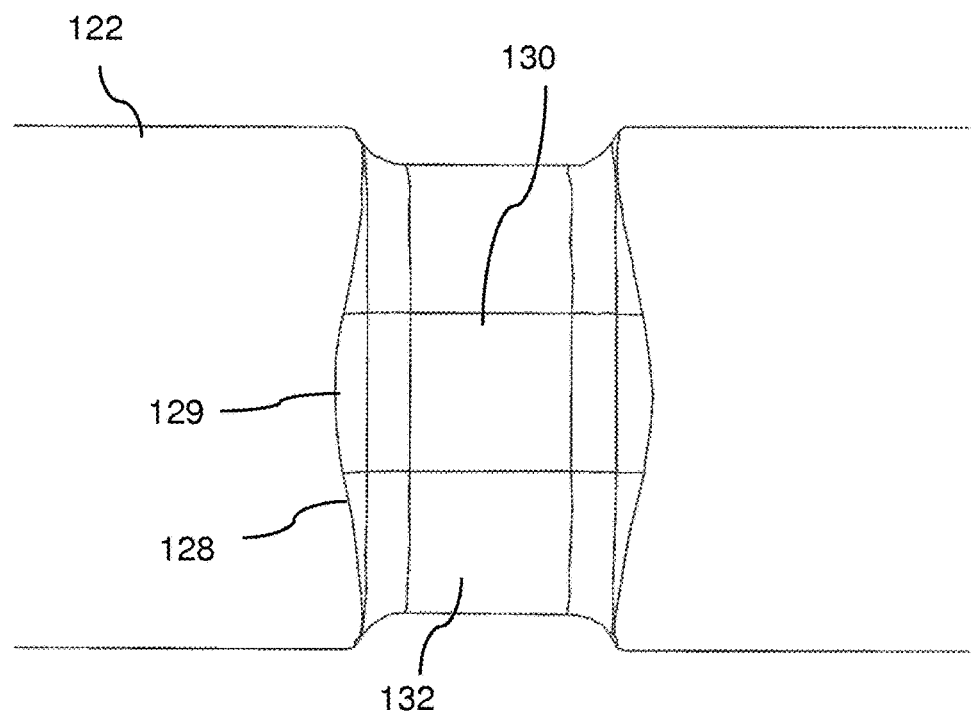
FIGS. 4A and 4B show enlarged views of the groove of FIG. 2 at various points of rotation.
Figure 4B:
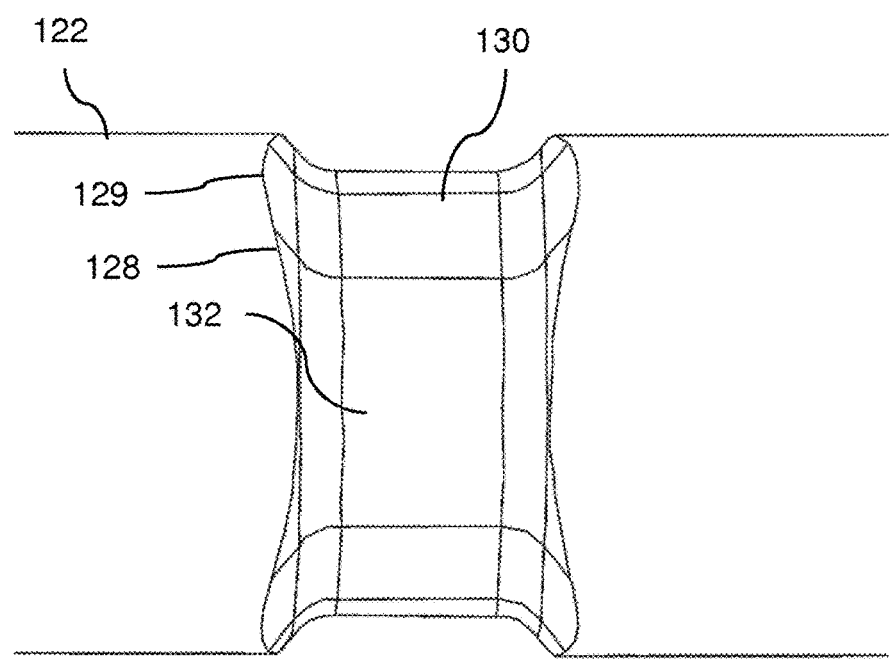

FIGS. 4A and 4B show enlarged views of the groove of FIG. 2 at various points of rotation. The groove is defined by a base and two opposing sloped walls 128 running circumferentially around the bur. Each ridge 122 is connected to the groove via a corresponding sloped wall 128. Each sloped wall 128 provides a ramp over which driving elements of coupling mechanism may pass to provide a smoother transition between ridges 122 and the groove 124 as the bur is inserted into the coupling mechanism.

The sloped walls 128 also provide additional sections for receiving torque from driving elements. Each sloped wall 128 comprises a sloped face 129 adjacent to each flat driving face 130. Each sloped face 129 is sloped relative to the longitudinal axis of the bur, at a constant gradient. Each sloped face 129 runs along a first direction that is perpendicular to the longitudinal axis. The first direction is also parallel to the corresponding flat driving face 130.

The radial distance of each sloped face 129 from the longitudinal axis increases a central (minimum) point outward when measured along the first direction. Accordingly, when a driving member makes contact with both sloped faces 129 it can drive the bur via the sloped faces in a similar manner to how the driving member can drive off of the flat driving face 130. In one arrangement, the bur is configured so that, for each indentation, a driving member can make contact and drive off of the flat driving face 130 and each of the sloped walls 129.

In addition, the sloped walls allow the channel 124 to set the longitudinal position of the bur. To allow this, the channel 124 is configured such that, when the driving elements are fully inserted into the channel 124, each driving element contacts both walls 128. This secures the bur, preventing any longitudinal movement, and allowing driving forces to be taken through both walls 128.

Figure 5:
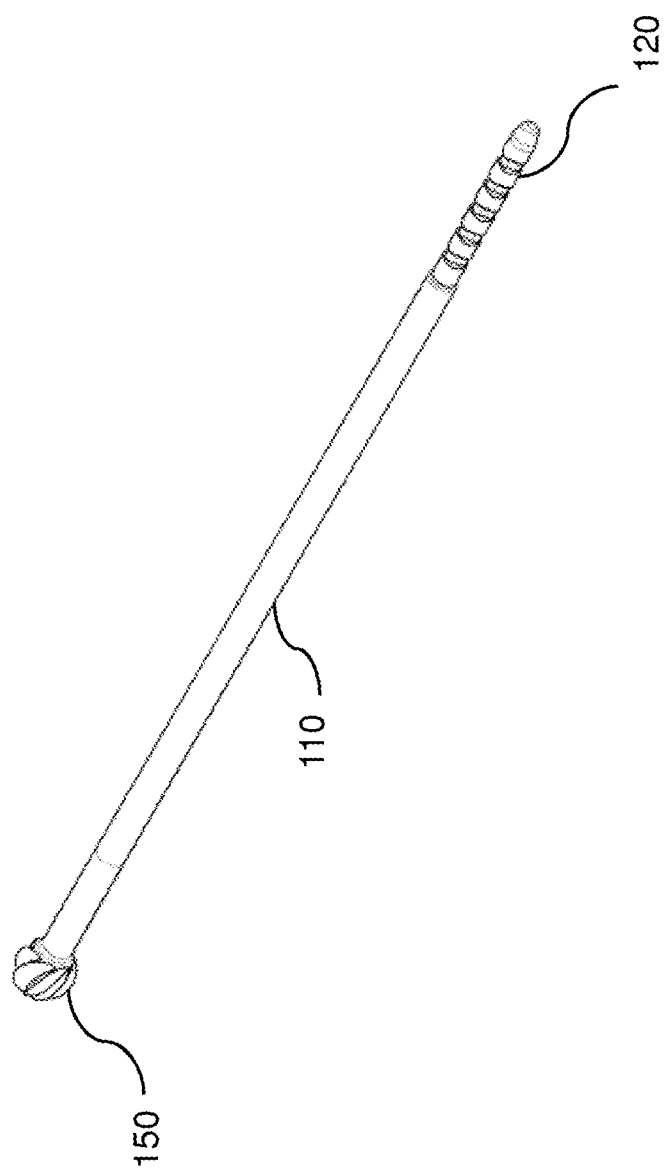
FIG. 5 shows a bur according to an alternative embodiment.

FIG. 5 shows a bur according to an alternative embodiment. This embodiment is much like the embodiment of FIG. 2; however, the coupling portion 120 comprises a plurality of grooves separated by ridges, the grooves and ridges alternating in the longitudinal direction up the coupling section 120. Each groove defines a position at which the bur may be coupled to a coupling mechanism. Accordingly, the coupling section 120 defines a plurality of selectable driving sections located along its length.

Figure 6A:
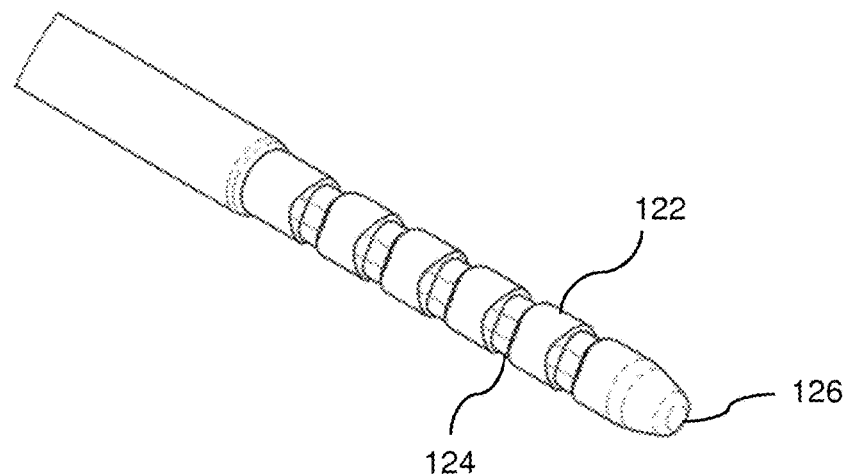
FIGS. 6A and 6B show enlarged views of the coupling section 120 of the bur of FIG. 5.
Figure 6B:
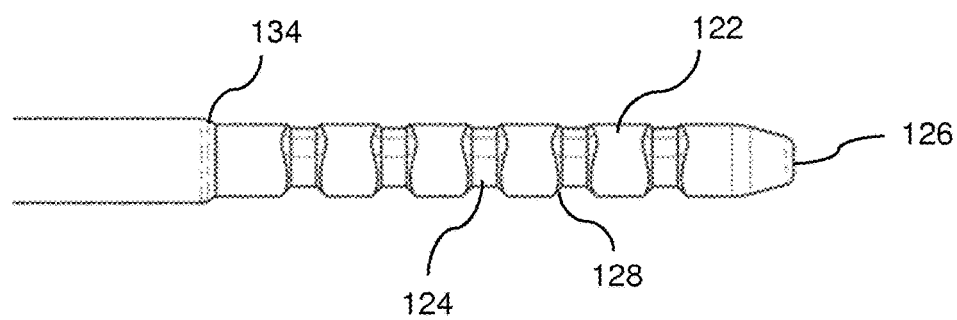
Figure 6C:
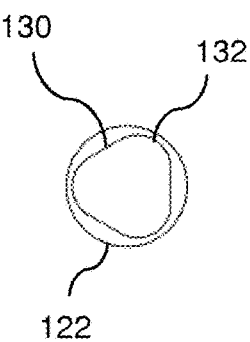
FIG. 6C shows a cross-sectional view of the coupling section 120 of FIG. 5.

FIGS. 6A and 6B show enlarged views of the coupling section 120 of the bur of FIG. 5. FIG. 6C shows a cross-sectional view of the coupling section 120 of FIG. 5. The ridges 122 and grooves 124 alternate along the length of the coupling section 120. Each groove 124 is the same shape as the groove 124 in the embodiment of FIG. 2, i.e. each groove has a triangular cross-section. The driving faces 130 of the grooves 124 are aligned with each other (i.e. the equivalent driving faces 130 of the grooves 124 are all angled at the same circumferential position) so that the bur does not need to be rotated when the longitudinal position of the bur is being changed. Various depths of grooves 124 (or heights of ridges 122) may be used based on the coupling requirements of the tool being secured.

Figure 7A:
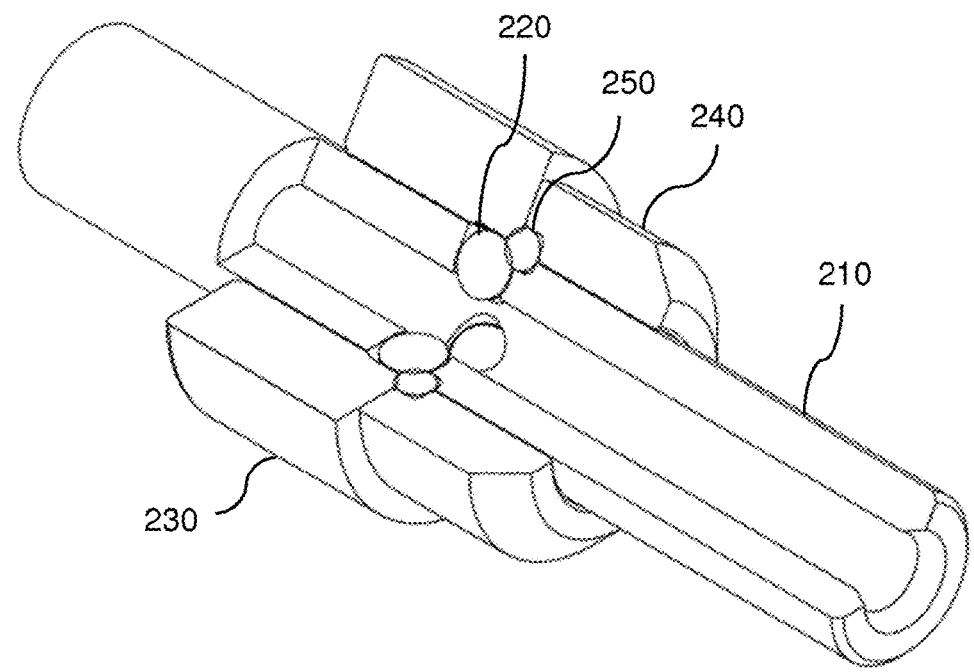
FIG. 7A shows a cut-away view of a coupling mechanism according to an embodiment.
Figure 7B:
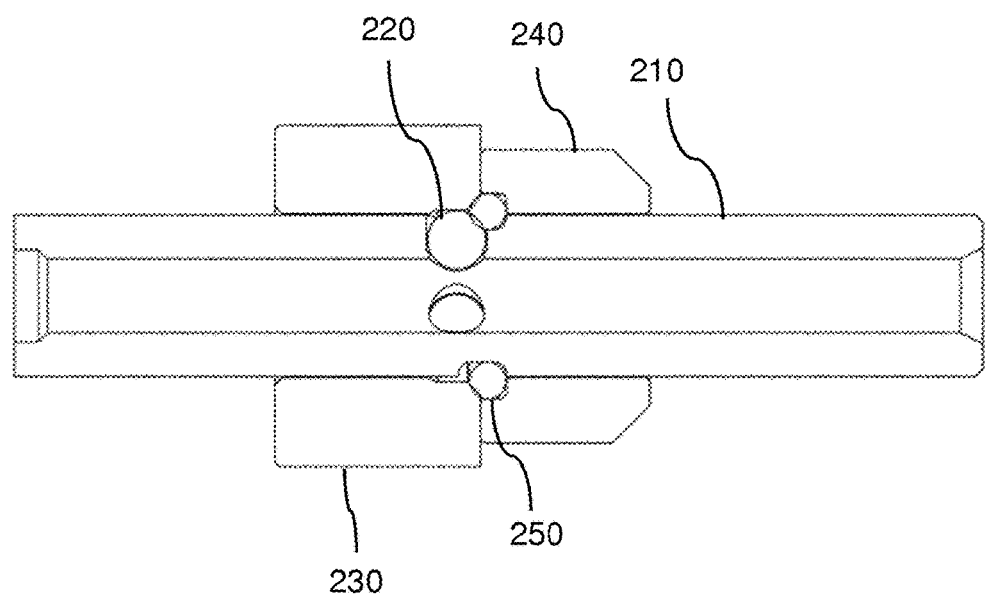
FIG. 7B shows a cross-section view of a coupling mechanism according to an embodiment.

FIG. 7A shows a cut-away view of a coupling mechanism according to an embodiment. FIG. 7B shows a cross-section view of a coupling mechanism according to an embodiment. The coupling mechanism comprises a sleeve 210 forming a central longitudinal cavity for receiving the coupling portion 120 of the bur. The sleeve 210 comprises three cavities each containing a corresponding ball 220. Each cavity passes into the sleeve 210 along a respective direction perpendicular to the longitudinal axis, that is, the cavities extend radially outwards from the central longitudinal cavity. The cavities are spaced around the sleeve 210 but are all located along a single plane perpendicular to the longitudinal axis.

The balls 220 and cavities are equally spaced circumferentially around the sleeve 210 at positions 120° from each other. The balls 220 are configured to secure and drive the bur via the driving faces 130 when the bur is inserted into the coupling mechanism.

The cavities include protrusions at the inner edge of the cavities to prevent the balls 220 falling into the central longitudinal cavity when the coupling mechanism is empty. The cavities in the sleeve 210 retain the balls 220 but allow the balls 220 to move radially at least partially out of the central longitudinal cavity. This allows the balls 220 to move out of the grooves 124 and over the ridges 122 of the coupling section 120 of the bur as the bur is moved into or out of the coupling mechanism to allow the balls 220 to be positioned in any of the grooves 124. This therefore provides a means of setting the longitudinal position of the bur within the coupling mechanism. The balls 220 are biased radially inwards by an O-ring 250 to provide some resistance to the bur as the balls 220 move out of the grooves 124 and over the ridges 122 and to urge the balls 220 into the grooves 124.

A locking ring 230 is located around the sleeve 210 at a proximal end of the sleeve 210. The locking ring 230 is configured to move longitudinally along the sleeve 210 and over the balls 220. When the locking ring 230 is retracted away from the balls 220, it is in an unlocked position wherein the balls 220 are free to move radially out of the longitudinal cavity to allow the bur to be slid into and out of the coupling mechanism.

On the opposite side of the cavity from the locking ring 230 is a second ring 240 encircling the sleeve 210. The second ring 240 includes a channel for the O-ring 250 to help secure the balls 220 within the coupling mechanism.

The locking ring 230 is configured to slide longitudinally from the unlocked position towards the second ring 240 and into a locked position over the balls 220 to urge the balls 220 inward. This provides a mechanism for locking the bur in position within the coupling mechanism. The locking ring 230 may be biased towards the locked position, for instance, via springs.

Figure 8:
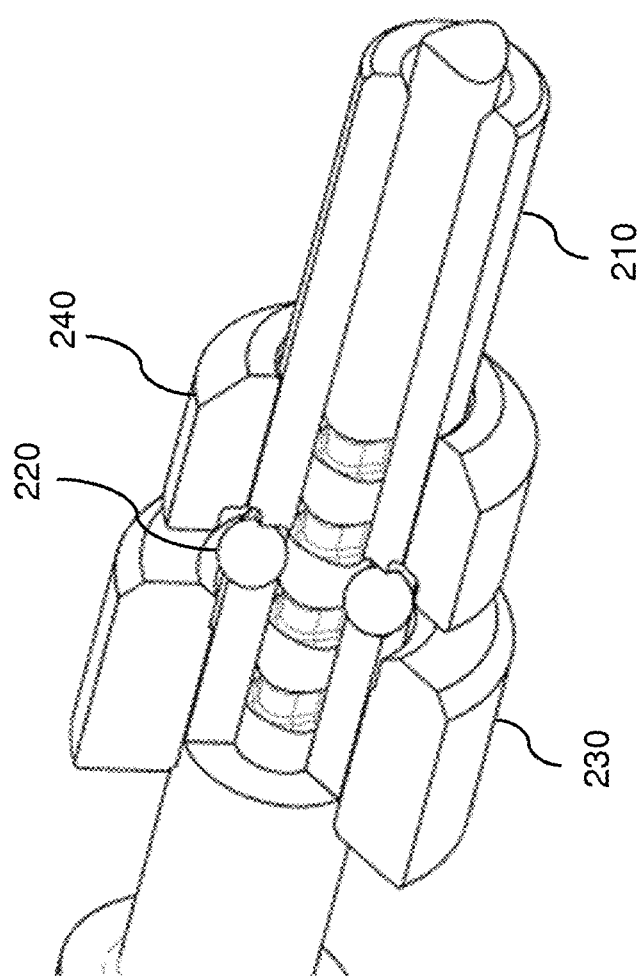
FIG. 8 shows a cutaway view of the bur inserted into the coupling mechanism in an unlocked arrangement.

FIG. 8 shows a cutaway view of the bur inserted into the coupling mechanism in an unlocked arrangement. The locking ring 230 is in a retracted (unlocked) position. There is therefore space above the balls 220 for the balls 220 to move radially outwards, into the cavity 232 in the sleeve 210. This provides space for the ridges 122 of the coupling section 120 to move past the balls 220. The bur may therefore be moved longitudinally within the coupling mechanism to insert the bur, remove the bur, or adjust the longitudinal position of the bur within the coupling mechanism. The bur may also be rotated 230 when the locking ring is in the unlocked position. Once the balls 220 are fully inserted within one of the grooves, the path will be free for the locking ring 230 to pass over the cavities to secure the balls 220 in position thereby locking the bur in place.

FIGS. 9A, 9B and 9C show cross-sectional views of the coupling mechanism with the bur inserted within the mechanism at various depths. As the locking ring 230 is in the unlocked position, the ball 220 is free to move upwards, into the cavity, to allow ridges 122 of the bur to move past it.

An O-ring 250 encircles the sleeve 210 within a circumferential channel on the inner surface of the second ring 240. The channel is located at the corner of the ring closest to the balls 220. This means that the O-ring 250 contacts each of the balls 220 and helps to urge the balls 220 radially inwards. The O-ring 250 therefore provides inwards pressure against the balls 220 when the mechanism is in the unlocked position. As the O-ring 250 extends partially into the cavity 232, it holds the balls 220 in place, preventing them from falling out of the coupling mechanism.

The downward pressure provided by the O-ring 250 to the balls 220 provides resistance when pushing the bur in and out, thereby providing a tactile feel for the different positions at which the bur can be located. The O-ring 250 is always in contact with the balls 220 to prevent any vibration in the mechanism. The O-ring 250 may be made from rubber, or some other elastic material.

In FIG. 9A, the bur has been inserted to a point where a ridge 122 is located directly underneath the ball 220. The ridge 122 has urged the ball 220 out of the central longitudinal cavity. The O-ring 250 provides resistance to this action as it is compressed by the ball 220.

In FIG. 9B, the bur has been pushed further into the coupling mechanism such that the ball 220 is now positioned above a groove 124. The ball 220 is urged into the groove 124 by the O-ring.

In the present case, the bur is rotated such that the ball 220 is positioned above one of the rounded corners 132 of the triangular cross-section of the groove 124. As the bur is rotated, the ball may be positioned deeper within the groove, as shown in FIG. 9C.

In FIG. 9C, the bur has been rotated such that the ball 220 is positioned above the centre point of one of the driving faces 130. Again, the O-ring 250 urges the ball 220 into the groove 124 until it is fully inserted into the groove 124. The ball 220 makes contact with the bur at three points of contact, the base of the groove 124, and the top edges of the sloped walls. This ensures that, once the coupling mechanism has been locked, the bur cannot move longitudinally, and provides a strong connection for the transfer of torque.

It can be seen from FIGS. 9B and 9C that the width of the groove 124 increases as the depth of the groove increases 124. This is due to the lengthening of the sloped walls, as the base has a constant width all around the bur. This means that, when the ball 220 is fully inserted into the groove 124, the sloped walls prevent the ball 220 from moving along the groove without the ball also moving radially outwards from the longitudinal axis. Accordingly, when the locking ring 230 is slid over the balls 220, the balls 220 are secured between the locking ring 230, the base of the groove 124 and the walls of the groove 124.

The sleeve 210 comprises a rim 212 protruding into the cavity from the inner end of the wall defining the cavity. This rim 212 forms an opening of reduced width/diameter relative to the cavity. The diameter of this opening is less than the diameter of the ball 220. This means that the opening of the cavity into the central longitudinal cavity is smaller than the diameter of the ball 220. This prevents the balls 220 from falling into the central longitudinal cavity when the coupling mechanism is empty.

Figure 10B:
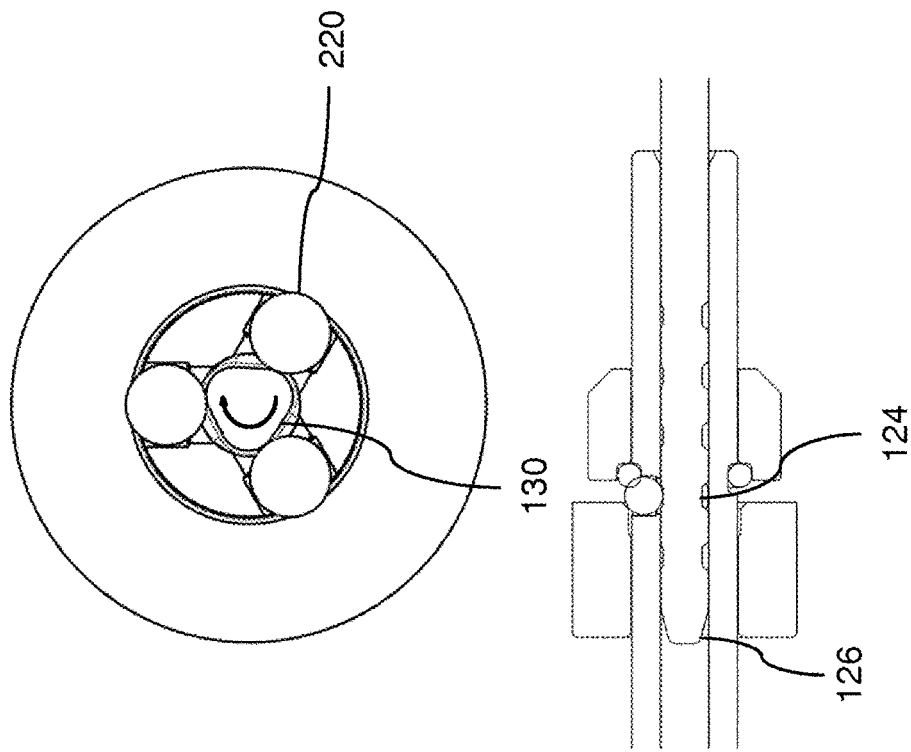
FIG. 10B shows cross-sectional views of the coupling mechanism within which a bur is inserted within, wherein balls are positioned above a groove of the bur.
Figure 10A:
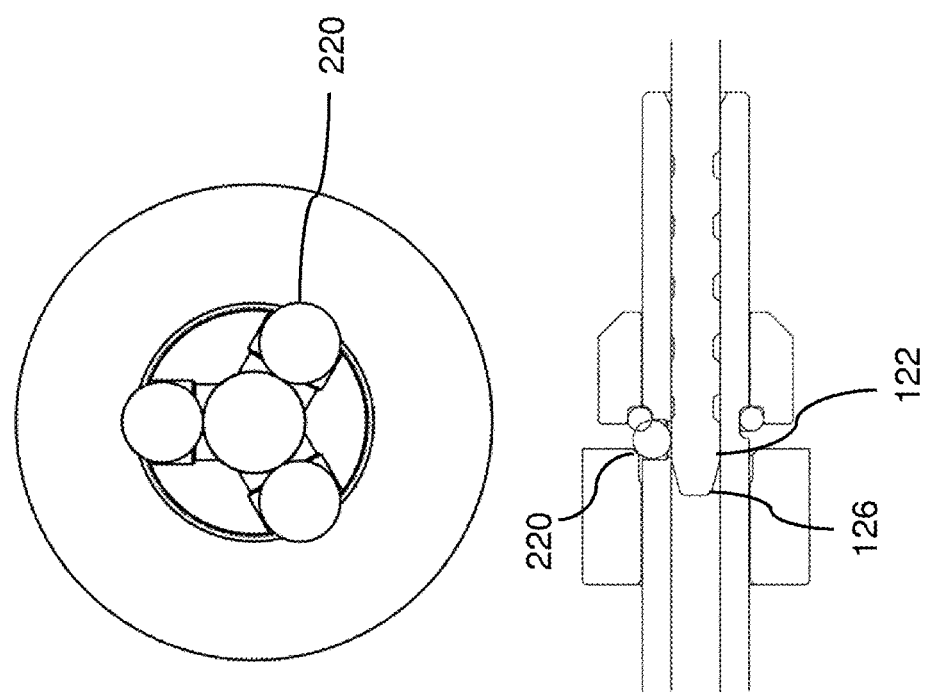
FIG. 10A shows cross-sectional views of the coupling mechanism within which a bur is partially inserted, wherein balls are positioned above a ridge of the bur.

FIG. 10A shows cross-sectional views of the coupling mechanism within which a bur is partially inserted, wherein the balls 220 are positioned above a ridge 122 of the bur. As the coupling mechanism is in an unlocked position, the balls 220 are free to move over the first ridge 122 of the bur to allow the bur to be inserted into the coupling mechanism. The conical tip 126 of the bur helps to ease the balls out of the path of the bur. As the conical tip 126 and ridges 122 have circular cross-sections, the bur may be inserted at any rotational alignment, and may be easily rotated when the balls 220 are positioned over these sections. As the bur is inserted further into the coupling mechanism, the balls 220 are able to slide and/or roll over the surface of the bur.

FIG. 10B shows cross-sectional views of the coupling mechanism within which a bur is inserted, wherein the balls 220 are positioned above a groove 124 of the bur. As the locking ring 230 is urged over the balls 220, the balls 220 are urged into the groove 124. The O-ring 250 provides additional inward force on the balls 220. Due to the triangular cross-section of the bur, the downward pressure placed on the balls 220 from the locking ring 230 and O-ring 250 causes a camming action causing the bur to naturally rotate until the balls 220 are able to sit on the lowest possible points, i.e. on the centres of the three driving faces 130.

In one arrangement, the locking ring 230 is urged over the balls 220 by a spring located behind the locking ring 230. This spring is contracted when the locking ring 230 is retracted so that it pushes the locking ring 230 back against the balls 220 when the locking ring 230 is released. This also helps secure the locking ring 230 in a locked position to prevent the device from unlocking when the bur is being driven.

The rounded corners of the triangular cross-section prevent the balls from locking into the wrong positon. Accordingly, the triangular cross-section and balls 220 cause the bur to automatically rotate around to the correct position.

Until the balls 220 are in the correct positon (on the centre of each driving face 130) they will protrude out of the sleeve. Accordingly, the locking ring 230 will push against the balls 220 when it is slid across the channel. This allows the locking ring 230 to provide additional force to urge the bur into correct alignment.

When the balls 220 are located within a groove 124, the balls 220 will naturally locate onto the correct flats of the bur, which will mean there is now room for the locking ring 230 to slide over the top of the balls 220 when the user wishes to lock the bur in place. When the mechanism is locked, the locking ring 230 prevents the balls 220 from moving radially outwards.

Figure 11A:
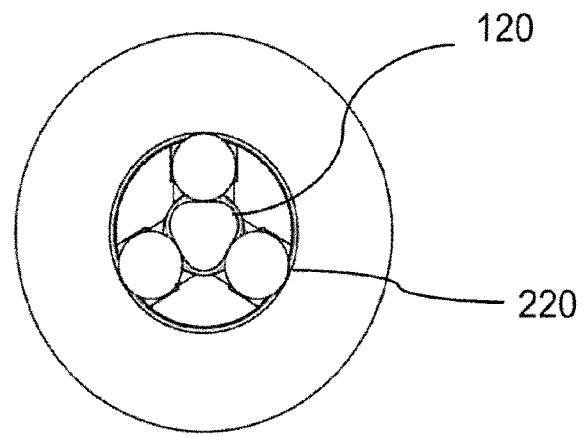
FIGS. 11A, 11B and 11C show cross-sectional views of the coupling mechanism with a bur locked within.
Figure 11B:
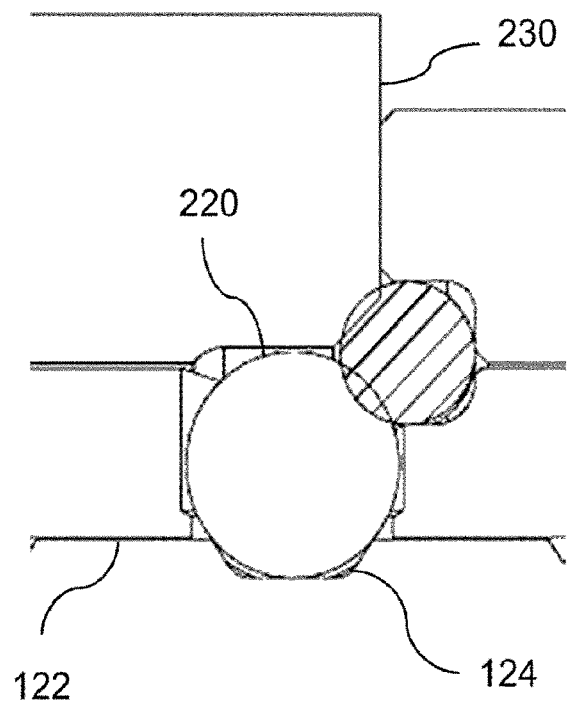
Figure 11C:
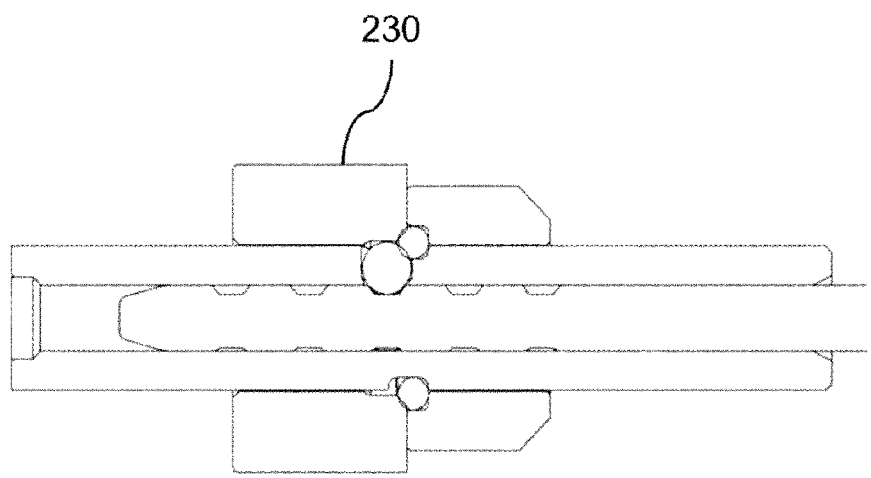

FIGS. 11A, 11B and 11C show cross-sectional views of the coupling mechanism with a bur locked within. The locking ring 230 is located in a locked position over the ball 220. This prevents the ball 220 from moving radially outward, away from the coupling section 120 of the bur. This urges the ball 220 into the groove 124 of the coupling section 220. The combination of the groove 124, the ridges 122 on either side of the groove 124, and the locking ring 230, means that the ball 220 is pinned and held within the groove 124. As the groove 124 has a triangular cross-section, the balls 220 are kept in place at the centre of the driving faces 130. The combination of the three balls 220 being pinned within their respective grooves 124 provides a secure clamping mechanism that allows the bur to be effectively driven.

The profile of the grooves 124 in which the balls 220 sit means that the bur cannot travel forward or backwards during use. This effect would be most prevalent when accelerating the tool or cutting with the tool as, during acceleration, the bur would naturally be urged forward. This can cause problems during high precision work, when the tool may jump forward when a surgeon accelerates it when attempting to make a cut. Accordingly, it is important to prevent any longitudinal slack in the coupling mechanism. The high tolerance gap of the present embodiment prevents any longitudinal movement of the bur as it matches the diameter of the ball 220 across the plane where the sloped walls make contact with the ball 220.

The coupling mechanism also acts as the drive mechanism to spin the bur. The coupling mechanism may be connected to a driving means, such as a motor, in order to drive the bur. The coupling mechanism may either be directly connected to the driving means or may be removably connected, e.g. where the coupling mechanism is located in a removable nosepiece that attaches to a handpiece comprising a motor. Due to the point contact between the balls 220 and the coupling section of the bur, the drive is very precise, and there is low friction between the balls 220 and the bur, which reduces the build-up of heat between the drive and the bur.

Whilst the above embodiments are described with three driving faces 130 and three balls 220, they may equally work with more faces 130 and balls 220. Having said this, the inventors have found that three faces 130 (and three balls 220) provide the best clamping arrangement as it provides as highly accurate way of evenly clamping the bur so it remains cylindrically accurate and that naturally self-centres. In addition, the use of three driving faces provides improved torque transfer whilst taking into account space restrictions on the locking mechanism and tool-piece. Providing rounded corners 132 between the driving faces 130 helps to prevent the mechanism from locking up.

Figure 12B:
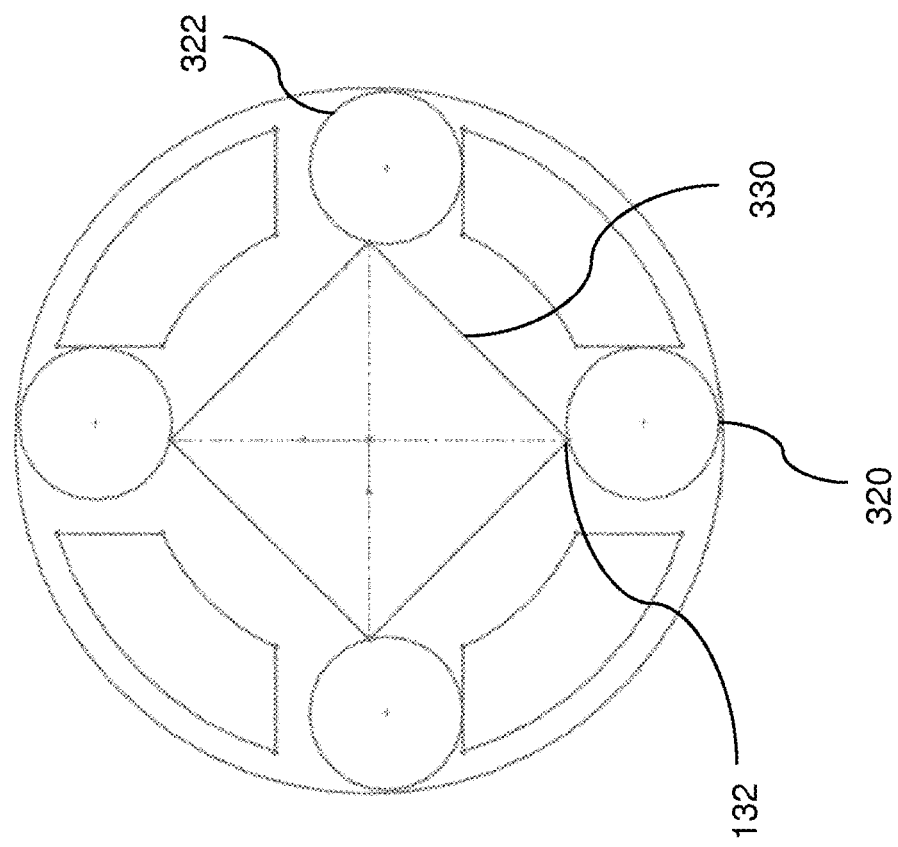
FIG. 12B shows a coupling arrangement with four points of contact and sharp corners.
Figure 12A:
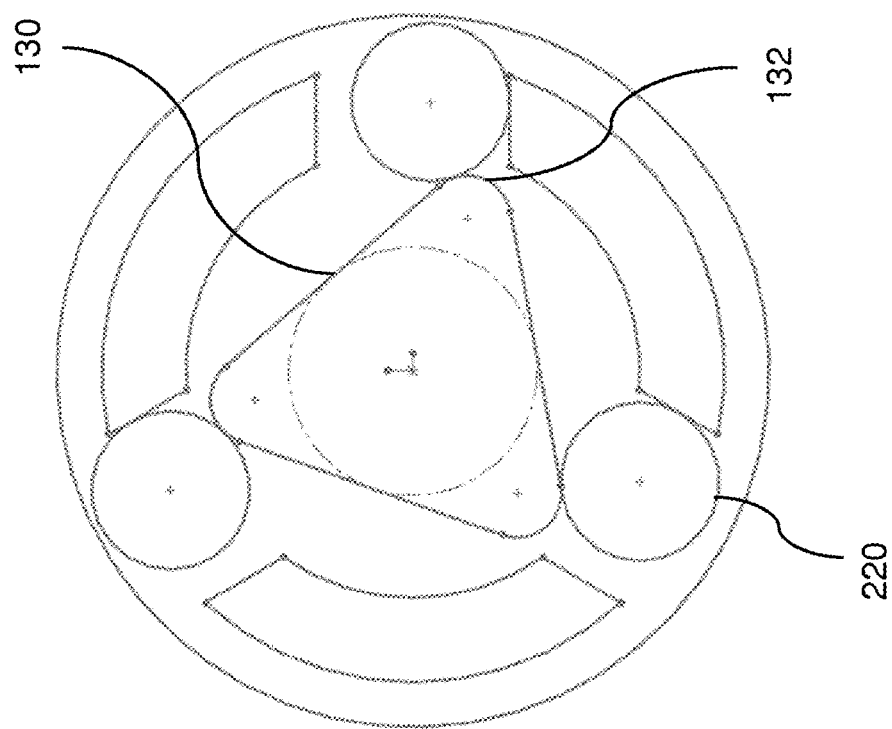
FIG. 12A shows a coupling arrangement with three points of contact and rounded corners.

FIG. 12A shows a coupling arrangement with three points of contact and rounded corners. FIG. 12B shows a coupling arrangement with four points of contact and sharp corners. It can be seen that if sharp corners are utilised there is a chance that inaccuracies in the manufacture of the parts could result in one or more of the balls 220 falling to the wrong side of the corners 132. In FIG. 12B, balls 320 and 322 are both being urged against the same driving face 330. Two balls 320, 322 locking on the same driving face 330 can result in the coupling mechanism partially locking/jamming in place. This would prevent the locking mechanism from auto-rotating to the correct orientation.

For this reason, some embodiments utilise rounded corners to avoid the coupling mechanism locking. Rounded corners also help to rotate the bur into position when the balls are urged against the corners.

Each groove 124 has sidewalls 128 and a base. The sidewalls 128 may be formed along a variety of angles relative to the base. Shallow angles make it easier for the balls 220 to roll over the ridges 122. In contrast, steeper angled walls 128 provide improved feedback to the user with regard to when the balls 220 are located within the grooves 124. Steeper walls also help to reduce the longitudinal slack between the bur and the locking mechanism.

Figure 13A:
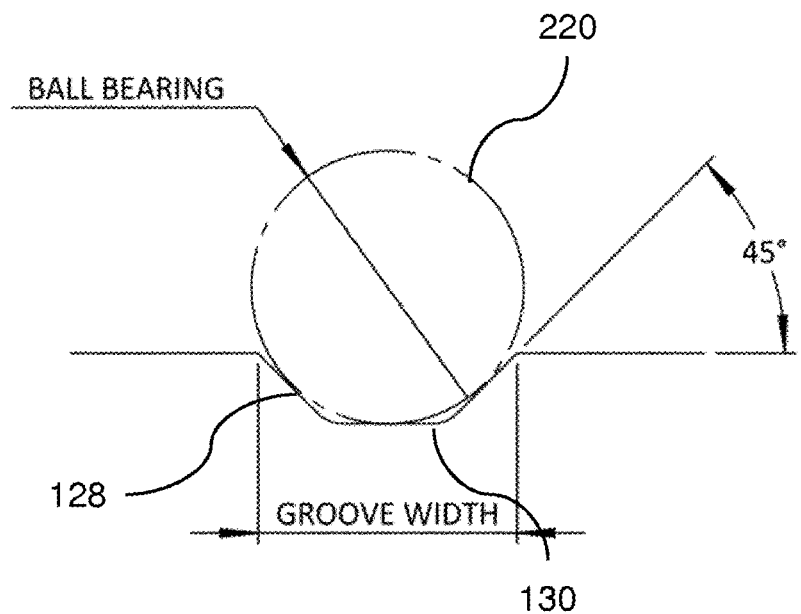
FIG. 13A shows a ball fitting within a groove with walls angled at 45° relative to the base of the groove.

FIG. 13A shows a ball 220 fitting within a groove 124 with walls 128 angled at 45° relative to the base of the groove 124. The base of the groove forms one of the driving faces 130. The sloped walls make it easier for the ball 220 to move over the ridges 122 when the system is in the unlocked arrangement. The ball 220 makes contact with the bur at three points of contact: at the base of the groove 124, and on each of the sloped walls 128. The ball 220 transfers torque to the bur via these three points of contact.

Figure 13B:
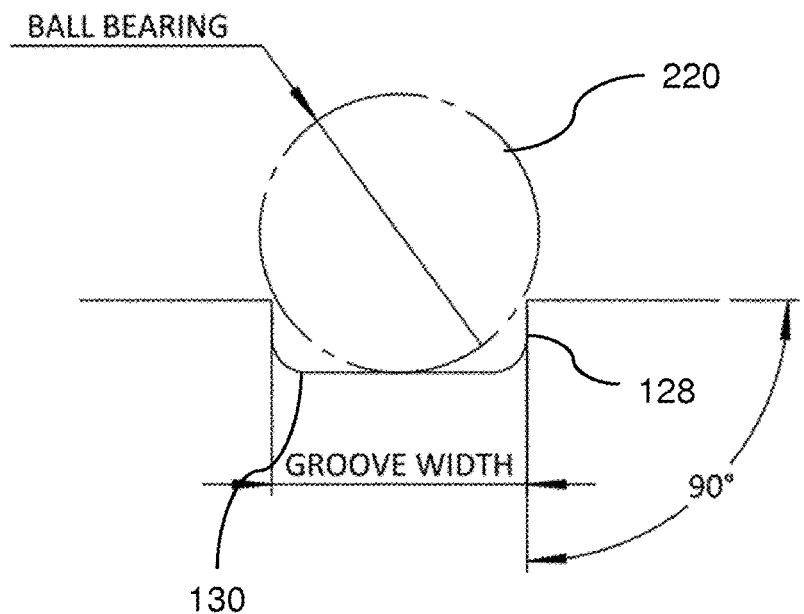
FIG. 13B shows a ball fitting within a groove with walls angled at 90° relative to the base of the groove.

FIG. 13B shows a ball fitting 220 within a groove 124 with walls 128 angled at 90° relative to the base of the groove 124. Each wall 128 is angled at 90° at its top edge, and forms a curved corner at its base to seamlessly join the wall 128 to the base of the groove 124. The walls 128 make contact with the ball 220 at the top edge of each wall 128.

In one embodiment, the walls 128 are angled at 55° relative to the base of the groove 124. This has been found to provide the best tactile feel when the coupling section 120 is moved in and out of the coupling mechanism. If the walls 128 are made steeper then it begins to become difficult to urge the balls 220 out of the grooves 124, any shallower and it becomes too easy and there is a reduced positive feel as the coupling section 120 is pushed in and out of the coupling mechanism.

The width of the groove 124 is chosen to ensure that the walls 128 secure the ball 220 and stop the bur from moving longitudinally forward or backwards during use. Accordingly, the channel 124 is configured such that the ball 220 is secured at three points of contact: the driving face 130 (base), and the top edges of the two walls 128. Nevertheless, this is not essential. Alternative embodiments secure each ball 220 between two points of contact in each groove 124, or one point of contact in each groove 124.

Whilst the above embodiments relate to burs specifically, the concepts described herein can equally be applied to securing and driving any rotational tool-piece.

As described above, a tool-piece may be provided with a coupling location comprising multiple indentations for the receipt of driving elements 220 for coupling the tool-piece to a driving mechanism. The indentations may be in the form of a single annular groove 124 or channel. The indentations may be sections of increased depth relative to the remainder of the groove 124. The walls 128 of the groove define a longitudinal location for the receipt of driving elements 220 whilst also providing points of contact to allow the driving elements to drive the tool-piece. The groove 124 therefore performs the dual purpose of longitudinally locating the tool-piece and allowing it to be driven effectively.

As described above, a tool-piece may be provided with multiple coupling locations spaced apart longitudinally along a coupling section 120 of the shaft. As multiple coupling locations are separated longitudinally along the shaft, the tool-piece can be selectively coupled at different locations along the shaft. This allows the tool-piece to be adjusted to suit the requirements of the user. In one embodiment, the tool-piece can be extended by up to 10 mm.

The adjustability of the coupling section 120 reduces the need for multiple tool-pieces of varying length to be acquired. This therefore provides a more adaptable and cost effective tool.

The cylindrical cross-section of the tip of the coupling section 120 and the ridges 122 means that the coupling section 120 can be loaded into the coupling mechanism in any rotational orientation. The grooves 124 comprise a set of three driving faces 130. This, coupled with the balls 220 that ride over the ridges 122, results in a cam function, which will automatically rotate the coupling section 120 into the correct orientation as the coupling mechanism is tightened up.

By providing three or more driving faces 130, the tool-piece may be more easily coupled to the coupling mechanism as it has a larger number of rotational orientations in which it may be secured. The additional driving faces 130 also help to further stabilise the tool-piece and provide a more effective connection for driving the tool-piece. The use of three balls 220 helps to centralise the tool-piece at high speeds. In contrast, securing a tool-piece at only two driving faces 130 would risk the tool-piece kicking to one side when it is being driven, resulting in vibration. This is because the tool-piece would only receive securing forces along one dimension (between the two faces), rather than in two dimensions due to the additional driving faces 130 in the present embodiments.

The combination of the rounded corners and driving faces 130 within a circumferential groove 124 means that the tool-piece auto aligns when driving elements are urged into the groove 124. This helps ensure that the tool-piece is correctly secured within the coupling mechanism. The fact that the corners are rounded prevents the tool-piece from locking in the incorrect position and jamming the tool-piece in place. The sloped walls 128 of the grooves 124 allows for tactile (positive feedback) of the different positions. The fact that each groove 124 runs around the entirety of the circumference of the coupling portion means that this feedback is provided even when the coupling elements are located over the rounded corners.

The use of driving elements that fit within indentations in the tool-piece (as opposed to, for instance, a collet system that clamps the tool-piece) means that there is improved torque transfer. The driving elements may be in the form of balls 220. This provides point drive contact, reducing the friction contact area and therefore reducing the build-up of heat. In addition, the balls 220 are able to roll over the surface of the coupling section 120 when the coupling mechanism is unlocked, thereby making it easier to move the tool-piece within the coupling mechanism.

The embodiments mentioned herein are descriptive of the invention, but may be modified without departing from the scope of the invention. For instance, it will be appreciated that the raised wall 134 shown in FIGS. 3A and 3B may be omitted in some embodiments, thereby resulting in a tool which has a shaft having the same radius as the coupling portion.

Equally, whilst the above embodiments comprise three driving elements 220 and an equivalent number of driving faces 130; however, alternative embodiments may include more than three driving elements 220 and more than three driving faces 130. There need not be the same number of driving elements 220 as driving faces 130, provided that each driving element 220 is able to be aligned with a corresponding driving face 130.

Whilst the above embodiments discuss the securing and driving of burs, the coupling mechanism described herein is suitable for securing and driving any tool that requires a rotational drive. This includes drills and burs and, in particular, surgical drills and burs.

Whilst the above embodiments discuss a coupling section comprising a groove, wherein a rotational drive may be taken through the driving faces 130 on the base of the groove 124, alternative embodiments can take the drive via the sloped side walls of the groove 124 only. In this case, no contact is made between the balls 220 and the base of the groove 124. The sloped side walls therefore provide both the functions of locating the tool longitudinally and driving the tool. This also means that the tool can adapt to the balls 220 wearing down through use.

As the base of the groove is recessed in this arrangement to avoid contact with the balls 220, the balls 220 can be inserted further into the groove as they wear down. As the balls 220 wear down, they will be urged deeper into the groove when being locked in place until they make contact with both side walls. If the movement of the balls 220 were to be limited instead by the depth of the channel, then this would risk the balls 220 being unable to move to a position where contact is made between both side walls. This could therefore affect the ability of the groove 124 to allow the tool to be secured longitudinally after the balls 220 have worn down. This arrangement therefore enables the tool to be driven effectively even after the balls 220 have undergone some wear.

Whilst certain embodiments have been described herein, the embodiments have been presented by way of example only, and are not intended to limit the scope of the inventions. Indeed, the novel methods and devices described herein may be embodied in a variety of other forms; furthermore, various omissions, substitutions and changes in the form of the methods and systems described herein may be made without departing from the scope of the invention as defined in the claims.

The invention claimed is:

1. A surgical tool-piece configured to be driven by a driving mechanism, the tool-piece comprising a shaft having a longitudinal axis running from a distal end of the shaft to a coupling portion at a proximal end of the shaft,
   wherein;
   the coupling portion comprises a driving section comprising at least three indentations located around a circumference of the coupling portion, each indentation being configured to receive a corresponding driving element of the driving mechanism to secure the surgical tool-piece both longitudinally and rotationally;
   each indentation is formed, at least partly, from respective distal and proximal walls configured to secure the surgical tool-piece longitudinally;
   each indentation comprises one or more surfaces, wherein each of the one or more surfaces is configured to receive a driving force to drive the surgical tool-piece to rotate around the longitudinal axis and wherein the one or more surfaces comprise a flat base of the respective indentation; and
   the distal and proximal walls for each indentation are joined to form a channel running around the circumference of the surgical tool-piece, the channel being formed from:
   the indentations; and
   channel sections linking adjacent indentations in the driving section, each channel section having a raised floor relative to its adjacent indentations to prevent the corresponding driving elements from moving along the channel, between indentations, without moving radially outwards, wherein each raised floor forms a rounded corner between the flat bases of adjacent indentations.

2. A surgical tool-piece according to claim 1, wherein each of the one or more surfaces defines a corresponding flat surface that passes along a first direction corresponding to the respective indentation, wherein the first direction is perpendicular to the longitudinal axis and the corresponding flat surface increases in radial distance from the longitudinal axis, when measured outward from a center point of the indentation along the first direction.

3. A surgical tool-piece according to claim 1, wherein the one or more surfaces comprise one or both of the distal and proximal walls.

4. A surgical tool-piece according to claim 1, wherein the distal and proximal walls are sloped at angles between 45° and 90° relative to the longitudinal axis.

5. A surgical tool-piece according to claim 1, wherein the distal and proximal walls are sloped at angles between 50° and 60° relative to the longitudinal axis.

6. A surgical tool-piece according to claim 1, wherein the distal and proximal walls are sloped at an angle of 55° relative to the longitudinal axis.

7. A surgical tool-piece according to claim 1, wherein the indentations form a triangular cross-section taken along a plane running perpendicular to the longitudinal axis and passing through the channel.

8. A surgical tool-piece according to claim 7 wherein the raised floors form rounded corners for the triangular cross-section.

9. A surgical tool-piece according to claim 1 wherein the coupling portion comprises a plurality of driving sections separated longitudinally from each other along the coupling portion to allow the tool-piece to be selectively coupled to the driving mechanism at different longitudinal positions along the coupling portion.

10. A surgical tool-piece according to claim 9 wherein the driving sections are separated by intermediate sections, wherein the intermediate sections have a circular cross-section taken along a plane running perpendicular to the longitudinal axis.

11. A kit of parts comprising a surgical tool-piece and a coupling mechanism, the surgical tool-piece configured to be driven by a driving mechanism, the tool-piece comprising:
a shaft having a longitudinal axis running from a distal end of the shaft to a coupling portion at a proximal end of the shaft, wherein:
the coupling portion comprises a driving section comprising at least three indentations located around a circumference of the coupling portion, each indentation being configured to receive a corresponding driving element of the driving mechanism to secure the surgical tool-piece both longitudinally and rotationally;
each indentation is formed, at least partly, from respective distal and proximal walls configured to secure the surgical tool-piece longitudinally;
each indentation comprises one or more surfaces, wherein each of the one or more surfaces is configured to receive a driving force to drive the surgical tool-piece to rotate around the longitudinal axis and wherein the one or more surfaces comprise a flat base of the respective indentation; and
the distal and proximal walls for each indentation are joined to form a channel running around the circumference of the surgical tool-piece, the channel being formed from:
the indentations; and
channel sections linking adjacent indentations in the driving section, each channel section having a raised floor relative to its adjacent indentations to prevent the corresponding driving elements from moving along the channel, between indentations, without moving radially outwards, wherein each raised floor forms a rounded corner between the flat bases of adjacent indentations; and
the coupling mechanism for securing the surgical tool-piece, the coupling mechanism comprising:
a sheath forming an internal longitudinal cavity for receiving the coupling portion of the tool-piece, the internal longitudinal cavity defining a central longitudinal axis of the coupling mechanism; and
at least three opposing coupling elements configured to secure the tool-piece in the coupling mechanism, each coupling element being located radially away from the central longitudinal axis and being configured to move radially outwards to allow at least part of the coupling portion of the tool-piece to pass the coupling element,
wherein the coupling mechanism is configured to urge the coupling elements radially inwards towards the central longitudinal axis to secure the tool-piece longitudinally and rotationally at corresponding indentations in the coupling portion of the tool-piece so that the tool-piece may be rotationally driven around the central longitudinal axis.

12. A surgical tool comprising a surgical tool-piece and a coupling mechanism, the surgical tool-piece configured to be driven by a driving mechanism, the tool-piece comprising:
a shaft having a longitudinal axis running from a distal end of the shaft to a coupling portion at a proximal end of the shaft, wherein:
the coupling portion comprises a driving section comprising at least three indentations located around a circumference of the coupling portion, each indentation being configured to receive a corresponding driving element of the driving mechanism to secure the tool-piece both longitudinally and rotationally;
each indentation is formed, at least partly, from respective distal and proximal walls configured to secure the surgical tool-piece longitudinally;
each indentation comprises one or more surfaces, wherein each of the one or more surfaces is configured to receive a driving force to drive the surgical tool-piece to rotate around the longitudinal axis and wherein the one or more surfaces comprise a flat base of the respective indentation; and
the distal and proximal walls for each indentation are joined to form a channel running around the circumference of the surgical tool-piece, the channel being formed from:
the indentations; and
channel sections linking adjacent indentations in the driving section, each channel section having a raised floor relative to its adjacent indentations to prevent the corresponding driving elements from moving along the channel, between indentations, without moving radially outwards, wherein each raised floor forms a rounded corner between the flat bases of adjacent indentations; and
the coupling mechanism for securing the surgical tool-piece, the coupling mechanism comprising:
a sheath forming an internal longitudinal cavity for receiving the coupling portion of the tool-piece, the internal longitudinal cavity defining a central longitudinal axis of the coupling mechanism; and
at least three opposing coupling elements configured to secure the tool-piece in the coupling mechanism, each coupling element being located radially away from the central longitudinal axis and being configured to move radially outwards to allow at least part of the coupling portion of the tool-piece to pass the coupling element,
wherein the coupling mechanism is configured to urge the coupling elements radially inwards towards the central longitudinal axis to secure the tool-piece longitudinally and rotationally at corresponding indentations in the coupling portion of the tool-piece so that the tool-piece may be rotationally driven around the central longitudinal axis.

* * * * *